(12) United States Patent
Gliner et al.

(10) Patent No.: US 9,974,608 B2
(45) Date of Patent: May 22, 2018

(54) DETERMINING ABSENCE OF CONTACT FOR A CATHETER

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 248 days.

(21) Appl. No.: 14/010,679

(22) Filed: Aug. 27, 2013

(65) Prior Publication Data
US 2015/0066021 A1   Mar. 5, 2015

(51) Int. Cl.
| A61B 18/14 | (2006.01) |
| A61B 5/00 | (2006.01) |
| A61B 17/00 | (2006.01) |
| A61B 18/00 | (2006.01) |
| A61B 5/053 | (2006.01) |
| A61B 90/00 | (2016.01) |

(52) U.S. Cl.
CPC ........ *A61B 18/1492* (2013.01); *A61B 5/6885* (2013.01); *A61B 5/0538* (2013.01); *A61B 2017/00725* (2013.01); *A61B 2018/00577* (2013.01); *A61B 2018/00869* (2013.01); *A61B 2018/00892* (2013.01); *A61B 2018/00904* (2013.01); *A61B 2018/00964* (2013.01); *A61B 2090/065* (2016.02); *A61B 2560/0223* (2013.01)

(58) Field of Classification Search
CPC ........... A61B 2018/00869; A61B 2018/00827; A61B 2018/00845
See application file for complete search history.

(56) References Cited

U.S. PATENT DOCUMENTS

| 6,226,542 B1 | 5/2001 | Reisfeld |
| 6,241,724 B1 | 6/2001 | Fleischman et al. |
| 6,301,496 B1 | 10/2001 | Reisfeld |
| 6,695,808 B2 | 2/2004 | Tom |
| 6,892,091 B1 | 5/2005 | Ben-Haim |
| 6,915,149 B2 | 7/2005 | Ben-Haim |
| 7,306,593 B2 | 12/2007 | Keidar et al. |

(Continued)

FOREIGN PATENT DOCUMENTS

| EP | 2 438 881 A1 | 4/2012 |
| EP | 2 574 278 A2 | 4/2013 |

(Continued)

OTHER PUBLICATIONS

EP Search Report dated Jan. 2015 EP 14 18 2246.

*Primary Examiner* — Linda Dvorak
*Assistant Examiner* — Bo Ouyang
(74) *Attorney, Agent, or Firm* — Vincent J. Serrao (57) ABSTRACT

A method, including injecting a current between an electrode of a catheter and tissue in proximity to the catheter, the catheter having a force sensor configured to measure a force between the catheter and the tissue. The method further includes measuring a succession of phase shifts of the current relative to a fixed reference and verifying that a cardinality of the measured phase shifts falling below a predetermined threshold increases over a predetermined time period. A zero-force point for the force sensor is calibrated according to the force measured by the force sensor during the predetermined time period.

18 Claims, 3 Drawing Sheets

(56) References Cited

U.S. PATENT DOCUMENTS

| | | |
|---|---|---|
| 7,481,809 B2 * | 1/2009 | Stern et al. .................... 606/41 |
| 7,497,858 B2 | 3/2009 | Chapelon |
| 7,536,218 B2 | 5/2009 | Govari |
| 8,981,914 B1 * | 3/2015 | Stetten .................. A61B 34/25 340/407.1 |
| 2006/0197525 A1 * | 9/2006 | Mens .................. G01R 33/565 324/307 |
| 2007/0070832 A1 | 3/2007 | Paikattu et al. |
| 2007/0100332 A1 | 5/2007 | Paul et al. |
| 2008/0275465 A1 | 11/2008 | Paul et al. |
| 2008/0288038 A1 | 11/2008 | Paul et al. |
| 2008/0312521 A1 * | 12/2008 | Solomon ....................... 600/374 |
| 2009/0093806 A1 | 4/2009 | Govari et al. |
| 2010/0298826 A1 * | 11/2010 | Leo et al. ........................ 606/41 |
| 2011/0184406 A1 * | 7/2011 | Selkee ............................ 606/41 |
| 2012/0108988 A1 * | 5/2012 | Ludwin ............... A61B 18/1492 600/508 |
| 2013/0085416 A1 * | 4/2013 | Mest ............................ 600/587 |

FOREIGN PATENT DOCUMENTS

| | | |
|---|---|---|
| EP | 2 397 099 A1 | 12/2014 |
| WO | WO 09/065140 A1 | 5/2009 |

\* cited by examiner

DETERMINING ABSENCE OF CONTACT FOR A CATHETER

CROSS-REFERENCE TO RELATED APPLICATION

This application is related to U.S. patent application titled "Determining Non-Contact State for a Catheter," filed on even date with the present application, and which is incorporated herein by reference.

FIELD OF THE INVENTION

The present invention relates generally to contact determination, and specifically to determination of absence of contact of a catheter with body tissue.

BACKGROUND OF THE INVENTION

In an ablation procedure on target tissue, such as the myocardium, verification of physical electrode contact with the target tissue, as well as measurement of the force or pressure of the contact, are important for controlling the delivery of ablation energy to the tissue. Attempts in the art to verify electrode contact with the tissue, and to accurately measure the contact force, have been extensive, and various techniques have been suggested. For example, U.S. Pat. No. 6,695,808, which is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724, which is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149, which is incorporated herein by reference. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332, which is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar at al., which is incorporated herein by reference, describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Saurav et al., which are incorporated herein by reference, describe an electrode catheter system having an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

injecting a current between an electrode of a catheter and tissue in proximity to the catheter, the catheter having a force sensor configured to measure a force between the catheter and the tissue;

measuring a succession of phase shifts of the current relative to a fixed reference;

verifying that a cardinality of the measured phase shifts falling below a predetermined threshold increases over a predetermined time period; and calibrating a zero-force point for the force sensor according to the force measured by the force sensor during the predetermined time period.

Typically, the cardinality is a strictly increasing function over the predetermined time period.

In a disclosed embodiment the succession of phase shifts includes a preset number of the measured phase shifts.

In a further disclosed embodiment the measured phase shifts falling below a predetermined threshold include phase shifts within a preset interval of possible values of the phase shifts. The method may further include, prior to verifying the cardinality of the measured phase shifts, determining values for the preset interval in a learning phase of the method.

In a yet further disclosed embodiment the method includes determining the fixed reference from a current versus time waveform generated by the current. Typically, measuring the succession of phase shifts includes comparing the current versus time waveform with a voltage versus time waveform generated by the current.

In an alternative embodiment calibrating the zero-force point includes automatically setting the zero-force point as the force measured by the force sensor. Alternatively, calibrating the zero-force point includes manually setting the zero-force point as the force measured by the force sensor.

There is further provided, according to an embodiment of the present invention apparatus, including:

a catheter having an electrode and a force sensor configured to measure a force between the catheter and tissue in proximity to the catheter; and a processor configured to:

inject a current between the electrode and the tissue, measure a succession of phase shifts of the current relative to a fixed reference, verify that a cardinality of the measured phase shifts falling below a predetermined threshold increases over a predetermined time period, and calibrate a zero-force point for the force sensor according to the force measured by the force sensor during the predetermined time period.

The present disclosure will be more fully understood from the following detailed description of the embodiments thereof, taken together with the drawings, in which:

DETAILED DESCRIPTION OF EMBODIMENTS

Overview

An embodiment of the present invention provides a simple, quick, and accurate method for determining if a force sensor of a catheter is in condition for zeroing. In other words, the method detects, with a probability of being correct of at least 99%, if a distal tip of the catheter, wherein the force sensor is located, is not in contact with body tissue, such as wall tissue of a heart chamber. The method may advantageously be used during an ablation procedure on the heart.

The method injects current between an electrode, herein also termed the ablation electrode, at the distal tip of the catheter and the body tissue. The ablation electrode may or may not be in contact with the tissue. Phase shifts of the injected current are measured relative to a fixed reference, the phase shifts varying depending upon whether or not the ablation electrode contacts the tissue. Typically, the phase shifts are measured from differences between a current waveform and a voltage waveform of the injected current.

The phase shifts are measured in an iterative manner, typically at a frequency of approximately 10 Hz, and the measurements are used to populate bins of a histogram of phase shifts. If there is a consistent increase, at every iteration, in the number of phase shift measurements below a predetermined phase shift threshold, typically in the lowest non-zero bin of the histogram, and if the consistent increase continues for more than a preset number of iterations, corresponding to a predetermined time period, then the force sensor is assumed to be out of contact with the tissue. In this case the force sensor may be calibrated, by assuming that the force reading of the force sensor is a zero-force point for the sensor.

The inventors have found that not only does the method detect, with an extremely high probability of being correct, if the sensor is in condition for zeroing, but also that the waiting time before such detection is very short. In one embodiment the preset number of iterations required for a consistent increase is four, so that since each iteration is of the order of tenths of seconds, the predetermined time period, i.e., the waiting time, is less than one second.

System Description

In the following description, like elements in the drawings are identified by like numerals, and the like elements are differentiated as necessary by appending a letter to the identifying numeral.

Figure 1:
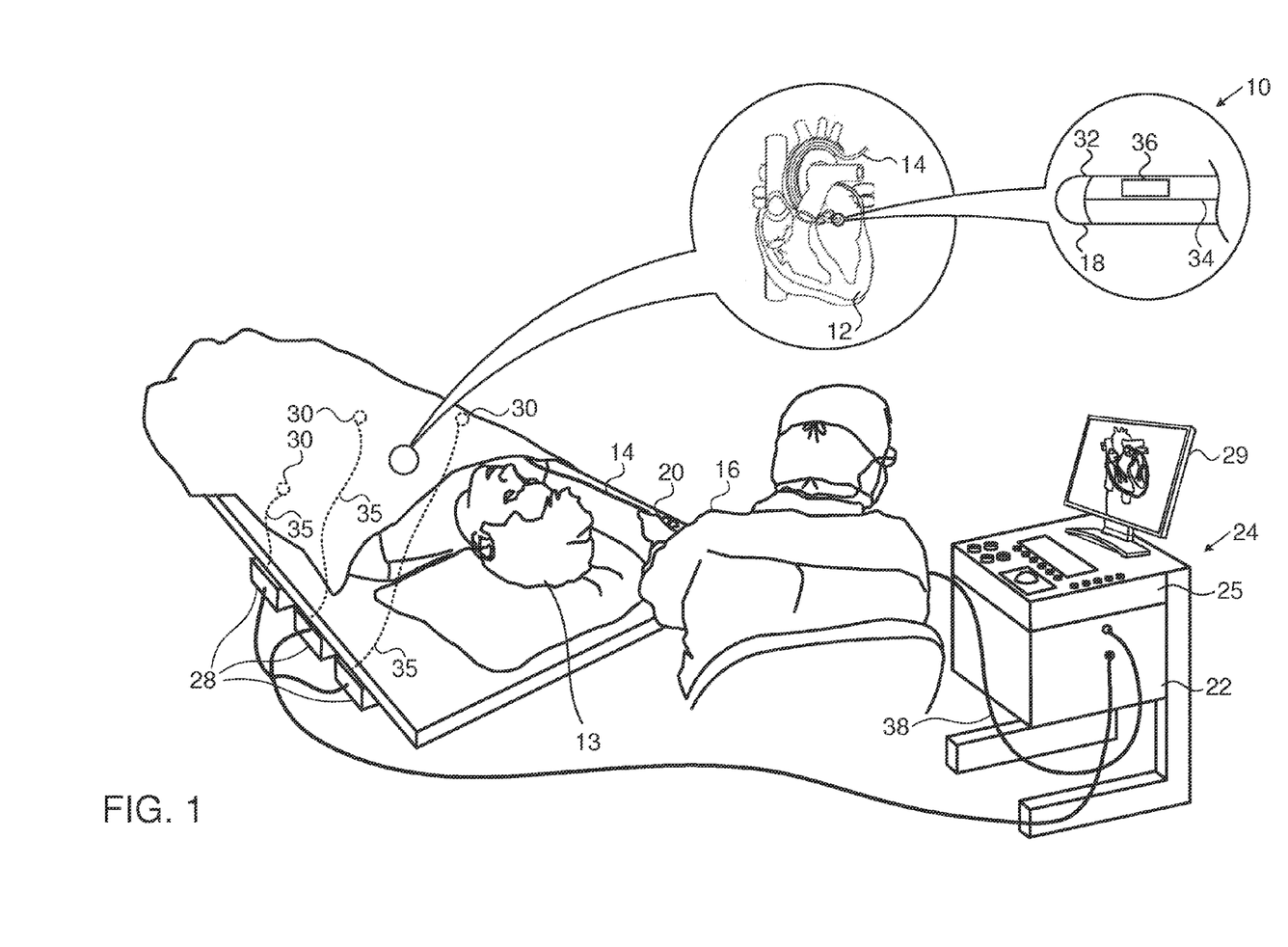
FIG. 1 is a pictorial illustration of a catheter system for performing ablative procedures on a heart of a living subject, according to an embodiment of the invention.

Reference is now made to FIG. 1, which is a pictorial illustration of a catheter system 10 for performing ablative procedures on a heart 12 of a living subject 13, according to an embodiment of the invention. The system comprises a catheter 14, which is percutaneously inserted by an operator 16 through the patient's vascular system into a chamber or vascular structure of the heart. The operator, who is typically a physician, brings the catheter's distal tip 18 into contact with the heart wall at an ablation target site, optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at distal tip 18, which apply the radiofrequency energy to the myocardium. The energy is absorbed in the tissue, heating it to a point (typically about 50° C.) at which it permanently loses its electrical excitability. This procedure creates non-conducting lesions in the cardiac tissue, which disrupt the abnormal electrical pathway causing the arrhythmia. The principles of the invention can be applied to different heart chambers to treat many different cardiac arrhythmias.

Catheter 14 typically comprises a handle 20, having suitable controls on the handle to enable operator 16 to steer, position and orient the distal end of the catheter as desired for the ablation. To aid the operator, the distal portion of catheter 14 may contain position sensors (not shown) that provide signals to a positioning processor 22, located in a console 24.

Ablation energy signals and other electrical signals can be conveyed to and from heart 12 through an electrode 32 located at distal tip 18 via a cable 34 to console 24. Electrode 32 may also be referred to herein as the ablation electrode. There may be other electrodes (not shown) located at the distal tip that are used for ablation. Pacing signals and other control signals may be conveyed from the console through cable 34 and electrode 32, or via the other electrodes at the distal tip, to the heart; these signals may be conveyed in parallel with any ablation energy signals, typically by using frequency multiplexing for the different signals.

Factors affecting the ablation generated by the ablation energy input to the tissue being ablated comprise, inter alia, the force applied to the tissue during the ablation process. In order to measure the force, the distal end of catheter 14 comprises a force sensor 36. Force or pressure sensors that are suitable for use in a catheter are well known in the art. For example, U.S. Patent Application Publications 2007/0100332 and 2009/0093806, whose disclosures are incorporated herein by reference, describe methods of sensing contact pressure between the distal tip of a catheter and tissue in a body cavity using a force or pressure sensor embedded in the catheter. However, force sensor 36 may comprise any other force or pressure sensor known in the art.

Wire connections 35 link the console with body surface electrodes 30 and other components of a positioning subsystem. Electrode 32 and body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near electrode 32.

Positioning processor 22 is an element of a positioning subsystem (of system 10) which measures location and orientation coordinates of catheter 14.

In one embodiment, the positioning subsystem comprises a magnetic position tracking arrangement that determines the position and orientation of catheter 14 by generating magnetic fields in a predefined working volume in the vicinity of the catheter, using field generating coils 28. These fields are sensed at the catheter and the sensed fields are used to determine positions and orientation coordinates for the catheter. Alternatively or additionally, the location of catheter 14 may also be determined using impedance measurements, as taught, for example in U.S. Patent Application Publication No. 2007/0060832, which is herein incorporated by reference. The positioning subsystem may be enhanced by position measurements using the impedance measurements described in the above-noted U.S. Pat. No. 7,536,218.

As noted above, catheter 14 is coupled to console 24, which enables operator 16 to observe and regulate the functions of the catheter. Console 24 includes a processor 25, preferably a computer with appropriate signal processing circuits, which operates system 10. Processor 25 is coupled to drive a monitor 29. The signal processing circuits typically receive, amplify, filter and digitize signals from catheter 14, including signals generated by the above-noted sensors and a plurality of location sensing electrodes (not shown) located distally in the catheter. The digitized signals are received and used by the console and the positioning subsystem to compute the position and orientation of catheter 14 and to analyze the electrical signals from the electrodes.

Figure 2:
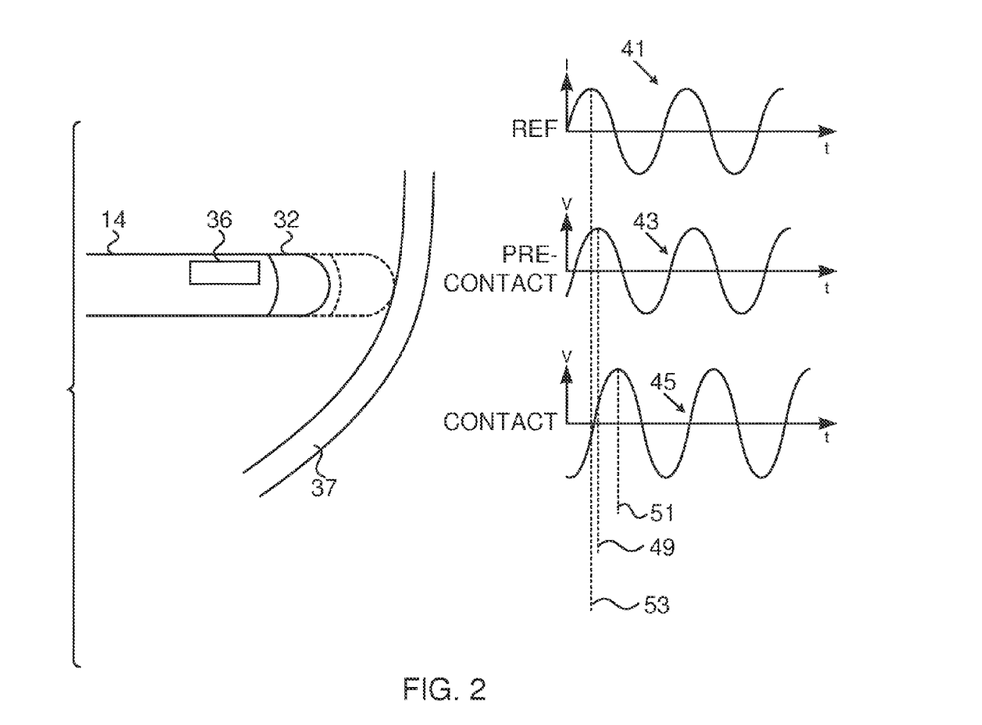
FIG. 2 is a composite drawing illustrating phase relationships of a current passing through an ablation electrode, according to an embodiment of the invention.

FIG. 2 is a composite drawing illustrating phase relationships of a current passing through ablation electrode 32, according to an embodiment of the invention. The current is typically separate from the ablation current passing through the ablation electrode, and since the current is used to ascertain if contact of the ablation electrode with the heart wall does or does not occur the current is also herein termed the contact determining current. The contact determining current passing ablation electrode 32 is an alternating current, having a phase shift which, as is described below, may be measured by comparing a current waveform with a voltage waveform generated by the current. The contact determining current through ablation electrode 32 is typically also used to make impedance measurements, so as to determine a location of the ablation electrode, as is described in above-referenced U.S. Patent Application Publication No. 2007/0060832 and U.S. Pat. No. 7,536,218.

As is described in more detail below, embodiments of the present invention measure changes in the phase shift of the contact determining current through ablation electrode 32 in order to determine whether or not there is contact between the ablation electrode and wall tissue 37 of heart 12.

Waveforms at the right side of FIG. 2 include, from top to bottom, a current (I) vs. time (t) waveform 41 of the contact determining current through electrode 32, a pre-contact voltage (V) vs. t waveform 43 for the current, taken when ablation electrode 32 is out of contact with wall 37, and a contact voltage (V) vs. t waveform 45 for the current, taken when the ablation electrode is in mechanical contact with wall 37.

The phase of current vs. time waveform 41 does not change substantially as the ablation electrode makes contact with the tissue. Waveform 41 may therefore be used as a fixed reference waveform for measuring the phase shift of the current passing through the ablation electrode or another tip electrode (not shown). It should be noted that ablation energy may be provided to the tissue while concurrently monitoring the phase shift. It is not necessary to interlace the two operations of providing ablation energy and monitoring the phase shift.

Phase shifts are indicated by displacement of vertical lines 49, 51 drawn through corresponding maxima of the pre-contact waveform 43 and the contact waveform 45. The phase shifts are measured with respect to the corresponding maximum of the reference waveform, indicated by a vertical line 53.

A change in phase shift occurs when ablation electrode 32 is brought into contact with wall 37. Furthermore, the phase shift increases on contact with wall 37, as is illustrated by waveforms 43 and 45. The inventors have discovered that phase shift measurement of this sort can be used not only to verify tissue contact, but also to ascertain with an extremely high degree of probability that contact is not occurring. While contact is not occurring, force sensor 36 may be zeroed.

Typically, during a medical procedure involving the measurement of force by sensor 36, the output of the sensor drifts, even though the force on the sensor may be constant. The drift is typically caused by changes in parameters of physical elements associated with the sensor, such as gain changes of amplifiers and/or dimensional changes of parts of the sensor. The drift may be compensated for by zeroing the sensor, but the zeroing should only be performed when there is no contact between the distal tip of the catheter and wall 37. Embodiments of the present invention provide system 10, and/or operator 16 of the system, with an indication than there is no contact between the catheter distal tip and any solid object, such as wall 37.

Figure 3:
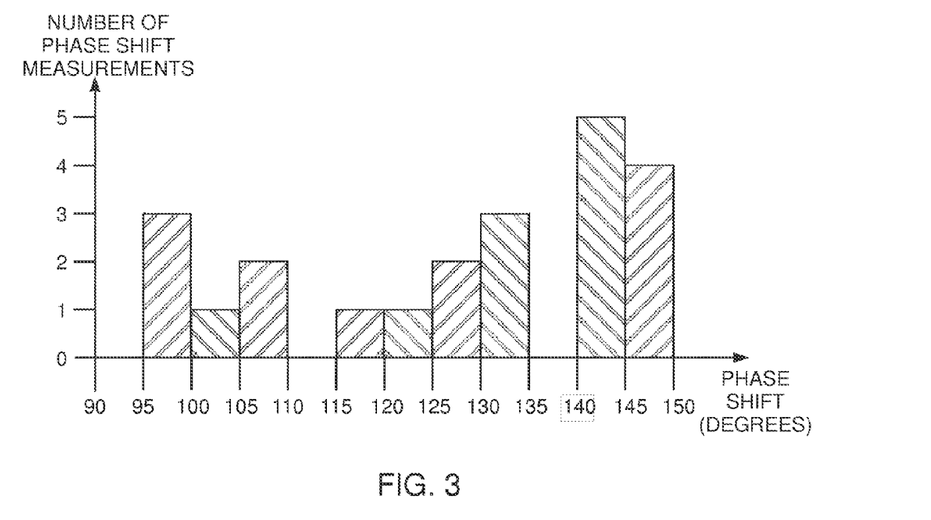
FIG. 3 is a schematic histogram generated by a processor, while the processor operates the system of FIG. 1, according to an embodiment of the present invention.

FIG. 3 is a schematic histogram generated by processor 25, while the processor operates system 10, according to an embodiment of the present invention. During operation of system 10, processor 25 evaluates the phase shift experienced by ablation electrode 32. The evaluation is performed on a repetitive basis, typically with a frequency at least equal to 10 Hz.

Processor 25 incorporates the evaluated phase shifts into a histogram of phase shifts. At the initial setup of system 10, the number of the bins of the histogram is typically preset. In one embodiment, illustrated in FIG. 3, there are 12 equal bins. The intervals for the bins are typically set dynamically, as is explained below. FIG. 3 illustrates the histogram having bins of 5° phase shift intervals, the phase shift of the histogram varying between a minimum of 90° to a maximum of 150°.

As the processor incorporates evaluated phase shifts into the histogram, it analyzes the histogram to determine if force sensor 32 is in a condition for zeroing. The method followed by the processor in building and analyzing the histogram is described with reference to the flowchart of FIG. 4.

Figure 4:
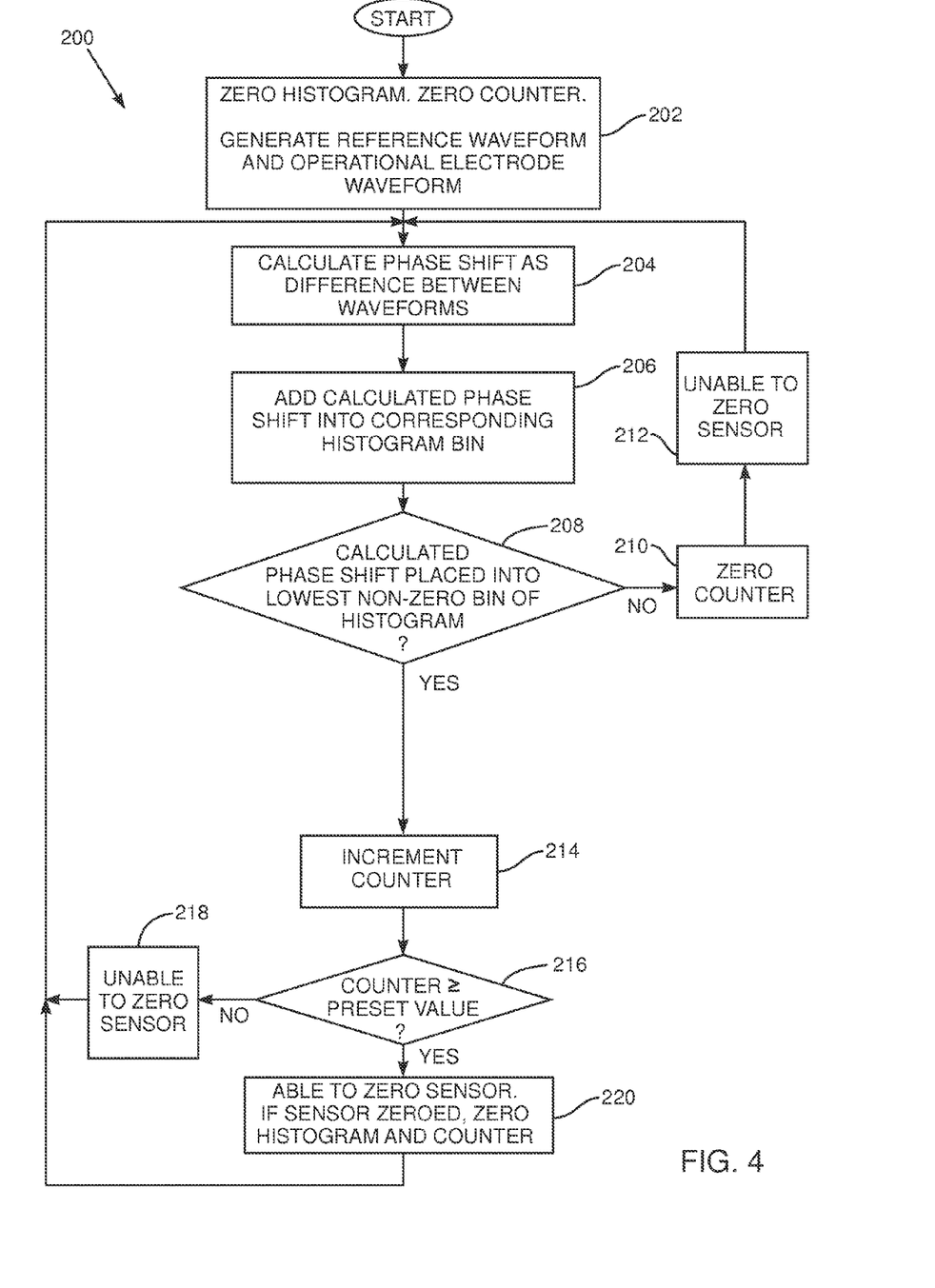
FIG. 4 is a flowchart of steps followed by the processor in operating the system of FIG. 1, according to an embodiment of the present invention.

FIG. 4 is a flowchart 200 of steps followed by processor 29 in operating system 10, according to an embodiment of the present invention. In an initial learning phase step 202, operator 16 sets parameters for the histogram of phase shifts, i.e., the number and size of the intervals of the histogram. Processor 25 zeroes the histogram by assuming that each of the intervals has a population of zero. In addition, processor 25 sets a zero-determining counter, the function of which is described below, to zero.

By injecting a current into ablation electrode 32, processor 25 respectively generates a reference waveform and an operational waveform. The reference waveform is typically a current vs. time waveform corresponding to reference waveform 41 (FIG. 2), and the operational waveform is typically a voltage time waveform corresponding to a waveform similar to waveforms 43 or 45.

During learning phase step 202 the processor calculates phase shifts for the injected current, and stores the phase shifts in a buffer. Typically, a number of phase shifts stored is approximately 100, although any other number may be used. Using the minimum and maximum values of the stored phase shifts, the processor calculates intervals for the histogram bins. For example, if the phase shifts vary between a minimum of 70° and a maximum of 100°, then the 12 bins of the histogram are set to cover the range of 70° to 100°, and each bin interval is set to be $$\frac{100-70}{12} = 2.5°.$$

Once the intervals of the bins have been set, the processor exits from learning step 202.

The remaining steps of the flowchart are performed iteratively, while system 10 is being operated. The iterations may be performed at a frequency of approximately 10 Hz, although any other convenient iteration frequency may be used. Typically, the iteration frequency is significantly faster than the frequency of the beating heart, which is approximately 2 Hz.

For each iteration of the flowchart, in a phase shift step 204, the processor calculates she phase shift for the operational waveform by calculating the difference between the reference and operational waveforms.

In a population step 206, the processor adds the calculated phase shift into the appropriate bin of the histogram.

In a first decision step 208, the processor determines if the phase shift calculated in step 206 has been added into the lowest non-zero, i.e., populated, bin of the histogram. For the first iteration of the flowchart, where all bins of the histogram are empty, the return from the decision is positive. For subsequent iterations the return depends on how the histogram is populated at the time of the decision step.

For example, if the histogram at the time of decision step 208 is as shown in FIG. 3, then the lowest non-zero bin of the histogram is the 95°-100° bin. Consequently, if the calculated phase shift in step 204 is in the interval 95°-100°, then the return is positive. If the calculated phase shift is in the interval 90°-95°, or in any of the intervals from 100° to 150°, then the return is negative. It will be understood that if the calculated phase shift is in the interval 90°-95°, then in the following iteration of the lowest non-zero bin of the histogram is the 90°-95° bin.

If the decision returns negative, then control continues to a counter setting step 210, wherein the processor sets the zero-determining counter to zero, and from there control passes to an unable-to-zero-sensor step 212.

In step 212 the processor assumes that the force sensor is not in a condition for zeroing, typically because the distal tip of the catheter may be contacting tissue of the heart. In some embodiments, where zeroing of the force sensor may be performed by operator 16 manually, step 212 includes providing an indication to the operator that the force sensor is not in a condition for zeroing. The indication may be visual, such as by providing a notice on screen 29 or changing the color of a button on the screen associated with the force sensor. Alternatively or additionally, the indication may use other operator senses, such as by having an auditory signal. From step 212 control returns to step 204, to initiate another iteration of the flowchart.

If decision step 208 returns positive, i.e., the number or cardinality of the lowest non-zero histogram bin increases, then control proceeds to an increment counter step 214, where the processor increments the zero-determining counter.

In a second decision step 216, the processor determines if the value of the zero-determining counter is equal to or greater than a preset value. In one embodiment the preset value is 4; however, other preset values may be determined without undue experimentation, and all such values are assumed to be within the scope of the present invention.

If step 216 returns positive, control continues to an able-to-zero-sensor step 220, wherein the processor assumes that she force sensor in a condition for zeroing, typically because she distal tip of the catheter is not contacting tissue of the heart. At this step the processor may zero the sensor automatically. Alternatively, the processor may provide an indication, such as a visual indication on screen 29, that the force sensor is in a condition for zeroing, and the operator may use this indication to manually zero the sensor. The zeroing of the force sensor comprises setting a zero-force point for the force sensor, as a calibration value, according to the force measured by the force sensor after decision step 216 returns positive. If the force sensor is zeroed, then the processor zeros the histogram, re-evaluates the intervals for the histogram, and zeroes the zero-determining counter, generally as described above for step 202.

From step 220, control returns to step 204 for another iteration of the flowchart.

If step 216 returns negative, control continues to an unable-to-zero-sensor step 218, which is substantially as described above for step 212. From step 218 control returns to step 204.

Consideration of flowchart 200 shows that processor 25 checks if there is a continuous increase in the number, i.e., the cardinality, of the lowest non-zero histogram bin for repeated iterations of the flowchart. In other words, the processor checks not only that the cardinality is a monotonically increasing function as the flowchart iterates, but that it is a strictly increasing function, i.e., increases in every iteration of the flowchart. The cardinality of the continuous increase is measured by the zero-determining counter. If there is a continuous increase, then once the counter reaches a preset value, the force sensor is assumed to be in condition for zeroing.

If there is no such continuous increase, i.e., if one of the iterations of the flowchart causes an increase in a non-lowest histogram bin, or creates a new lowest non-zero histogram bin, then the cardinality of the analyzed lowest non-zero histogram bin is not a strictly increasing function. In this case the zero-determining counter is automatically reset to zero and the force sensor is assumed not to be in condition for zeroing.

While the description above has assumed that processor 25 constructs a histogram similar to that illustrated in FIG. 3, it will be understood that physical construction of such a histogram is not necessary. Rather, processor 25 may maintain in a memory associated with the processor values equivalent to histogram values, i.e., ordered pairs of (a phase shift interval, a cardinality of the phase shift interval), and the processor may use such ordered pairs to evaluate all the steps of flowchart 200.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for measuring force while compensating for drift, comprising:
   injecting a current between an electrode of a catheter and tissue in proximity to the catheter, the catheter comprising a force sensor configured to measure a force between the catheter and the tissue;
   measuring in succession, a plurality of phase shifts of the current relative to a fixed reference;
   populating one or more bins of a histogram of the phase shifts;
   determining a condition for zeroing by verifying that a cardinality of the measured phase shifts in a particular bin falling below a predetermined threshold increases over a predetermined time period; and
   compensating for drift during the condition for zeroing by calibrating a zero-force point for the force sensor according to the force measured by the force sensor during the predetermined time period.

2. The method according to claim 1, wherein the cardinality is a strictly increasing function over the predetermined time period.

3. The method according to claim 1, wherein the succession of phase shifts comprises a preset number of the measured phase shifts.

4. The method according to claim 1, wherein the measured phase shifts falling below a predetermined threshold comprise phase shifts within a preset interval of possible values of the phase shifts.

5. The method according to claim 4, and comprising, prior to verifying the cardinality of the measured phase shifts, determining values for the preset interval in a learning phase of the method.

6. The method according to claim 1, and comprising determining the fixed reference from a current versus time waveform generated by the current.

7. The method according to claim 6, wherein measuring the succession of phase shifts comprises comparing the current versus time waveform with a voltage versus time waveform generated by the current.

8. The method according to claim 1, wherein calibrating the zero-force point comprises automatically setting the zero-force point as the force measured by the force sensor.

9. The method according to claim 1, wherein calibrating the zero-force point comprises manually setting the zero-force point as the force measured by the force sensor.

10. Apparatus for measuring force while compensating for drift, comprising:
    a catheter comprising an electrode and a force sensor configured to measure a force between the catheter and tissue in proximity to the catheter; and
    a processor configured to:
      inject a current between the electrode and the tissue,
      measure, in succession, a plurality of phase shifts of the current relative to a fixed reference,
      populate one or more bins of a histogram of the plurality of phase shifts,
      determine a condition for zeroing by verifying that a cardinality of the measured phase shifts falling below a predetermined threshold increases over a predetermined time period, and
      compensate for drift during the condition for zeroing by calibrating a zero-force point for the force sensor according to the force measured by the force sensor during the predetermined time period.

11. The apparatus according to claim 10, wherein the cardinality is a strictly increasing function over the predetermined time period.

12. The apparatus according to claim 10, wherein the succession of phase shifts comprises a preset number of the measured phase shifts.

13. The apparatus according to claim 10, wherein the measured phase shifts falling below a predetermined threshold comprise phase shifts within a preset interval of possible values of the phase shifts.

14. The apparatus according to claim 13, wherein the processor is further configured to determine values for the preset interval in a learning phase of the method prior to verifying the cardinality of the measured phase shifts.

15. The apparatus according to claim 10, wherein the processor is configured to determine the fixed reference from a current versus time waveform generated by the current.

16. The apparatus according to claim 15, wherein the processor is further configured to measure the succession of phase shifts comparing the current versus time waveform with a voltage versus time waveform generated by the current.

17. The apparatus according to claim 10, wherein the processor is further configured to calibrate the zero-force point the processor automatically setting the zero-force point as the force measured by the force sensor.

18. The apparatus according to claim 10, wherein the processor is further configured to calibrate the zero-force point upon an operator of the apparatus manually setting the zero-force point as the force measured by the force sensor.

\* \* \* \* \*